(12) United States Patent
Sartor et al.

(10) Patent No.: US 7,628,787 B2
(45) Date of Patent: Dec. 8, 2009

(54) SELF CONTAINED, GAS-ENHANCED SURGICAL INSTRUMENT

(75) Inventors: Joe D. Sartor, Longmont, CO (US); Michael Hogan, Boulder, CO (US); Gene H. Arts, Berthoud, CO (US); Ronald J. Podhajsky, Boulder, CO (US); Arlan J. Reschke, Boulder, CO (US)

(73) Assignee: Covidien AG, Neuhausen am Rheinfall (CH)

(*) Notice: Subject to any disclaimer, the term of this patent is extended or adjusted under 35 U.S.C. 154(b) by 856 days.

(21) Appl. No.: 11/048,577

(22) Filed: Feb. 1, 2005

(65) Prior Publication Data
US 2005/0171528 A1 Aug. 4, 2005

Related U.S. Application Data

(60) Provisional application No. 60/541,326, filed on Feb. 3, 2004.

(51) Int. Cl.
*A61B 18/14* (2006.01)
(52) U.S. Cl. .................................................. 606/41
(58) Field of Classification Search ............... 606/41, 606/46, 48–50
See application file for complete search history.

(56) References Cited

U.S. PATENT DOCUMENTS

| | | | |
|---|---|---|---|
| 2,708,933 A | 5/1955 | August | |
| 2,828,747 A | 4/1958 | August | |
| 3,434,476 A | 3/1969 | Shaw et al. | |
| 3,569,661 A | 3/1971 | Ebeling | |
| 3,692,973 A | 9/1972 | Oku et al. | |
| 3,699,967 A | 10/1972 | Anderson | |
| 3,832,513 A | 8/1974 | Klasson | |
| 3,834,433 A * | 9/1974 | Thompson | ............ 141/392 |
| 3,838,242 A | 9/1974 | Goucher | |
| 3,903,891 A | 9/1975 | Brayshaw | |
| 3,970,088 A | 7/1976 | Morrison | |
| 3,987,795 A | 10/1976 | Morrison | |
| 3,991,764 A | 11/1976 | Incropera et al. | |
| 4,014,343 A | 3/1977 | Esty | |
| 4,019,925 A | 4/1977 | Nenno et al. | |

(Continued)

FOREIGN PATENT DOCUMENTS

| | | |
|---|---|---|
| DE | 3710489 | 11/1987 |
| DE | 4139029 | 6/1993 |
| DE | 4326037 | 2/1995 |
| DE | 9117019 | 4/1995 |
| DE | 195 37 897 | 3/1997 |
| DE | 9117299 | 4/2000 |

(Continued)

OTHER PUBLICATIONS

U.S. Department of Labor—Occupational Safety & Health Administration, Regulations (Standards—29 CFR), p. 2.*

(Continued)

*Primary Examiner*—Michael Peffley
*Assistant Examiner*—Ronald J Hupczey, Jr.

(57) ABSTRACT

An electrosurgical apparatus for coagulating tissue includes an elongated housing and an electrode located adjacent the distal end of the housing. The electrode can be connected to a source of electrosurgical energy. At least one actuator is included which electrosurgically energizes the electrode. The apparatus also includes a relatively small gas cylinder which contains a pressurized gas consisting of inert gas and which is selectively seated in the housing. Upon actuation of the actuator, gas is dispersed under pressure from the gas cylinder to the electrode and is ionized prior to the distribution of the gas into the operating field.

33 Claims, 2 Drawing Sheets

U.S. PATENT DOCUMENTS

| | | | |
|---|---|---|---|
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmonesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Brown et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,700,260 A | 12/1997 | Cho et al. |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,141,985 A * | 11/2000 | Cluzeau et al. ............ 62/293 |
| 6,149,648 A | 11/2000 | Cosmescu |
| 6,197,026 B1 | 3/2001 | Farin et al. |
| 6,206,878 B1 * | 3/2001 | Bishop et al. ............ 606/49 |
| 6,213,999 B1 | 4/2001 | Platt, Jr. et al. |
| 6,264,650 B1 | 7/2001 | Hovda et al. |
| 6,348,051 B1 | 2/2002 | Farin et al. |
| 6,458,125 B1 | 10/2002 | Cosmescu |
| 6,475,217 B1 | 11/2002 | Platt |
| 6,558,383 B2 | 5/2003 | Cunningham et al. |
| 6,616,660 B1 | 9/2003 | Platt |
| 6,666,865 B2 | 12/2003 | Platt |
| 6,852,112 B2 | 2/2005 | Platt |
| 2001/0018587 A1 | 8/2001 | Yamamoto |
| 2002/0022838 A1 | 2/2002 | Cunningham et al. |
| 2003/0093073 A1 | 5/2003 | Platt |
| 2003/0144654 A1 | 7/2003 | Hilal |
| 2004/0088029 A1 | 5/2004 | Yamamoto |
| 2005/0015086 A1 | 1/2005 | Platt |
| 2005/0070894 A1 | 3/2005 | McClurken |

FOREIGN PATENT DOCUMENTS

| | | |
|---|---|---|
| DE | 19848784 | 5/2000 |
| DE | 29724247 | 8/2000 |
| EP | 0 447 121 A2 | 9/1991 |
| EP | 0 612 535 | 8/1994 |
| EP | 956827 | 11/1999 |
| EP | 1 090 599 | 4/2001 |
| EP | 1 127 551 A1 | 8/2001 |
| EP | 1 561 430 A1 | 8/2005 |
| EP | 1 570 798 A2 | 9/2005 |
| EP | 1 595 507 A2 | 11/2005 |
| FR | 1340509 | 9/1963 |
| GB | L014995 | 12/1965 |
| JP | 61-159953 | 7/1986 |
| SU | 1438745 | 11/1988 |
| WO | WO91/13593 | 9/1991 |
| WO | WO93/03678 | 3/1993 |
| WO | WO 96/24301 | 8/1996 |
| WO | WO96/27337 | 9/1996 |
| WO | WO 01/62333 | 8/2001 |
| WO | WO 02/058762 | 8/2002 |
| WO | WO 2005/016142 | 2/2005 |

OTHER PUBLICATIONS

International Search Report EP 06 01 9572 dated Nov. 21, 2006.
European Search Report for EP 05002257.3 Dated Jun. 1, 2005.
Extended European Search Report for European Patent Application No. EP 07 00 4356 dated Jul. 2, 2007 (7 pages).
Grund et al., "Endoscopic Argon Plasma . . . Flexible Endoscopy" Surgery and Allied Technologies, No. 1, vol. 2, pp. 42-46 (Feb. 1994).

Farin et al., "Technology of Argon Plasma . . . Endoscopic Applications" Endoscopic Surgery and Allied Technologies, No. 1, vol. 2, pp. 71-77 (Feb. 1994).

Brand et al., "Electrosurgical Debulking of Ovarian Cancer: A New Technique Using the Argon Beam Coagulator" Gynecologic Oncology 39 pp. 115-118 (1990).

Hernandez et al., "A Controlled Study of the Argon Beam Coagultor for Partial Nephrectomy" The Journal of Urology, vol. 143, May (J. Urol. 143: pp. 1062-1065, 1990).

Ward et al., "A Significant New Contribution to Radical Head and Neck Surgery" Arch Otolaryngology, Head and Neck Surg., vol. 115 pp. 921-923 (Aug. 1989).

Mark H. Mellow, "The Role of Endoscopic Laser Therapy in Gastrointestinal Neoplasms" Advanced Therapeutic Endoscopy, pp. 17-21.

Silverstein et al., "Thermal Coagulation Therapy for Upper Gastrointestinal Bleeding" Advanced Therapeutic Endoscopy, pp. 79-84.

Way et al., "Techniques in Therapeutic Endoscopy" W.B. Saunders Company, Philadelphia, PA., pp. 1.7-1.15.

International Search Report 01102843.8-2305.

International Search Report PCT/US98/19284.

European Search Report.

\* cited by examiner

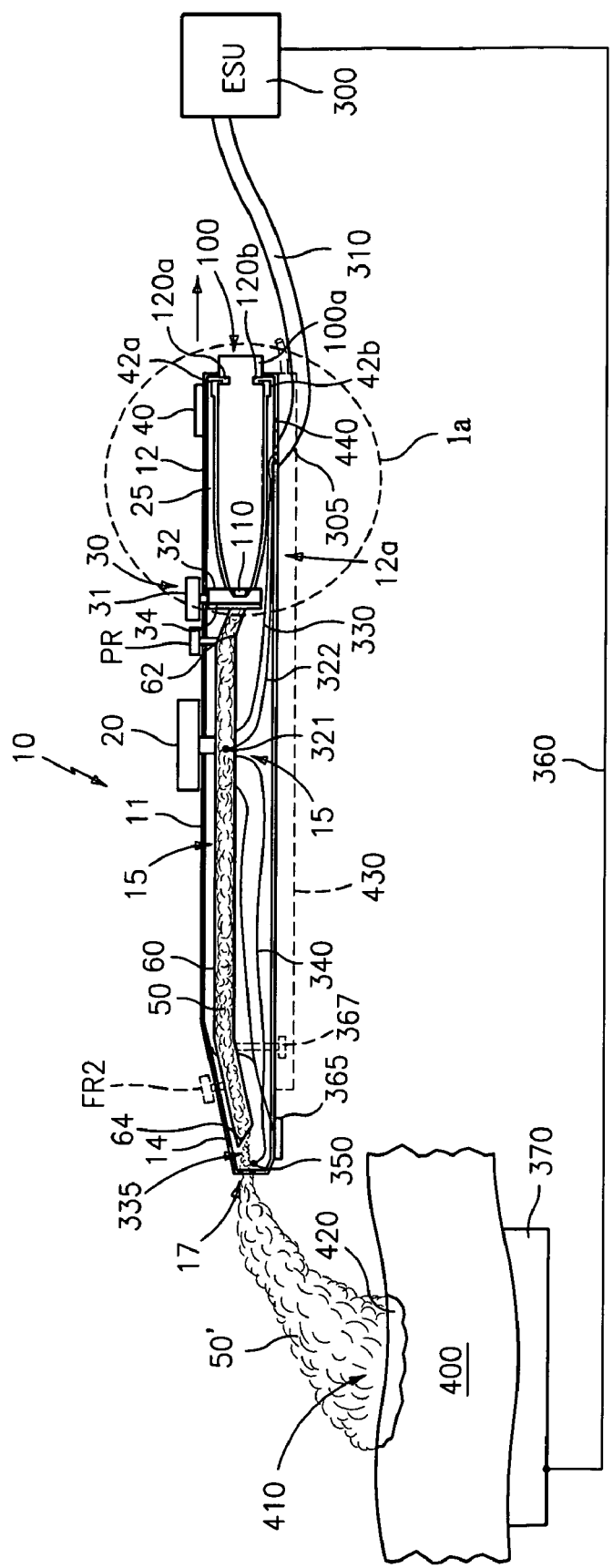
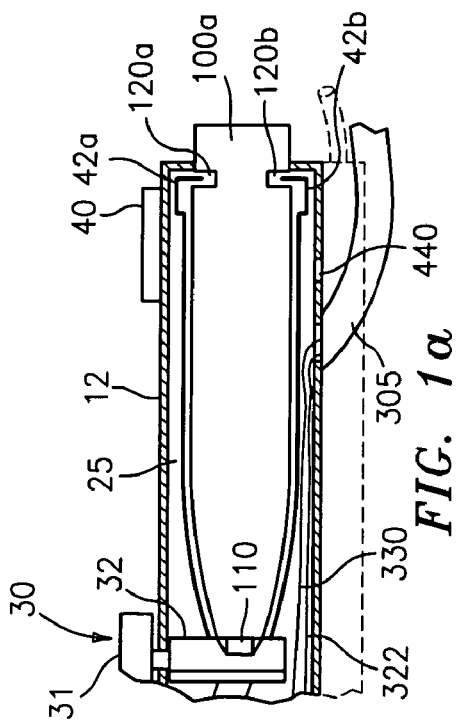
FIG. 1
FIG. 1a

SELF CONTAINED, GAS-ENHANCED SURGICAL INSTRUMENT

CROSS REFERENCE TO RELATED APPLICATION

This application claims the benefit of priority to U.S. Provisional Application Ser. No. 60/541,326 entitled "SELF CONTAINED, GAS-ENHANCED SURGICAL INSTRUMENT" filed on Feb. 3, 2004 by Joe Don Sartor, the entire contents of which being incorporated by reference herein.

BACKGROUND

The present disclosure relates to devices for use in open, laparoscopic or endoscopic procedures for treating tissue. More particularly, the present disclosure relates to gas-enhanced surgical instruments, including electrosurgical instruments for treating tissue, which include a self-contained and/or selectively replaceable gas supply for use during medical or surgical applications.

BACKGROUND OF RELATED ART

Devices, hereafter understood to include instruments for treating tissue, for example, for tissue division, dissection, ablation, or for arresting blood loss and coagulating tissue are well known. For example, several prior art instruments employ thermic coagulation (heated probes) to arrest bleeding. However, since the probe must come into close contact with the bleeding tissue, the probe may adhere to the tissue during probe removal and may possibly cause repeat bleeding. Many surgical probes also produce an undesirable buildup of eschar on or proximate the probe tip which detrimentally affects the efficiency of the surgical instrument. Other instruments direct high frequency electric current through the tissue to stop bleeding. Again, eschar adherence may occur with these instruments. In addition, with both types of instruments, the depth of the coagulation is often difficult to control.

One or more prior art devices have attempted to resolve certain of the above-noted and other problems by providing a tube-like coagulation instrument in which an ionizable gas, for example argon gas, is supplied from a remote gas container or tank to the instrument and ionized by an electrode prior to the gas being emitted from the distal end of the instrument towards the bleeding tissue. Other instruments have been developed which include an electrode for ionizing a stream of remotely provided ionizable gas which exits the distal end of the instrument at a rate of less than about 1 liter/minute. Providing the gas at this flow rate is believed to effectively cloud the tissue area and create an ionizable gas "atmosphere" to gently coagulate the tissue. The atmosphere of ionized gas is beneficial, for example, because it helps focus an arc of energy adjacent the electrode and it displaces oxygen from the area and reduces oxidative stress of the tissue.

It is thought that electrosurgical instruments which utilize ionizable gas to effectively coagulate tissue all utilize a gas hose (or other hose-like connection) to connect the instrument to a remote, removable large gas tank or gas container for use during the operation. Typically, the gas supply or source is situated in close proximity to the operating room where the gas is stored for repeated use during the operation and subsequent operations. As can be appreciated, having a gas supply hose attached to the electrosurgical instrument can be distracting to surgeons, burdensome (especially during intense and complicated surgical procedures, e.g., those utilizing multiple instruments simultaneously) and prone to entanglement or interference with the other electrosurgical cords attached to the instrument(s). Thus, a need exists to develop a self-contained, gas-enhanced electrosurgical instrument and small cylinders of pressurized gas utilizable therewith which eliminate the need for gas hoses and remotely located and large gas storage containers. Electrosurgical instruments according to this disclosure include a self-contained, replaceable, small gas cylinder of pressurized inert gas (preferably argon gas, or mixture of inert gases) which provide advantages over the use of prior large, remote containers of ionizable gas for various generic uses, including for dispersing debris or fluid at surgical sites.

The instruments and small containers of the present disclosure are easy to handle and manipulate. These instruments may be configured to include one or more of a variety of features, e.g., flow and/or pressure regulators, pressure relief valves, gauges, indicators, sensors and control systems that can be tailored to fit the surgical procedure. The instruments and the controls associated therewith may be controlled by hand and in sight by the user which accordingly, provide the opportunity for obtaining optimized results. The small containers and their contents can also be tailored, e.g., in terms of use of a particular inert gas or gas mixture, gas pressure, volume, flow rate, etc., to fit the particular instrument and/or procedure, thereby also providing the opportunity for obtaining optimized results.

SUMMARY

An electrosurgical instrument for providing ionized inert gas to a surgical site includes a frame having a proximal end and a distal end, the distal end having a port for emitting gas, a receptacle for seating a cylinder of pressurized gas therein, a cylinder seated in the receptacle and containing pressurized gas consisting of inert gas, an active electrode located adjacent the distal end of the frame, the electrode being adapted to connect to a source of electrosurgical energy, a channel for channeling the pressurized gas to the proximity of electrode, and at least one actuator for actuating the flow of pressurized inert gas from the cylinder to the active electrode, and for actuating the delivery of electrosurgical energy from the source to the active electrode for ionizing the inert gas for use at the surgical site.

In one embodiment, the at least one actuator actuates the flow of pressurized gas and also operates as an actuator which actuates the delivery of the electrosurgical energy. In another embodiment, the at least one actuator can be adapted to actuate the release of pressurized gas from the cylinder prior to actuating the delivery of the electrosurgical energy. In yet another embodiment, a first actuator actuates the flow of pressurized gas from the cylinder and a second actuator actuates the delivery of the electrosurgical energy from the source to the active electrode.

It is contemplated that one or more elements may be utilized to actuate the first actuator prior to actuating the second actuator. The at least one actuator for actuating the flow of pressurized gas can comprise a valve. The cylinder may include a sealed outlet and the valve may include a coupling for engaging and breaking the seal of the cylinder. The valve can include a plenum positioned between the coupling and the channel for limiting flow of pressurized gas to the channel. The valve can comprise a pressure regulator for regulating the pressure of the gas. A pressure regulator may be included to regulate the pressure of the gas that flows to the proximity of the active electrode separate and proximal to the valve activating flow to the electrode. The regulation of pressure may be achieved with a single regulator attached to the cylinder or with the addition of a second regulator for lower and/or more precise control of the pressure. A first flow regulator may be included which selectively regulates the flow of pressurized gas from the cylinder, and, optionally, a second flow regulator may be included which selectively regulates the flow of pressurized gas to the electrode to below a selected level.

In one embodiment, the at least one actuator which actuates the flow of pressurized inert gas from the cylinder, and which actuates the delivery of electrosurgical energy, is selectively adjustable to selectively adjust the flow of pressurized gas and the delivery of electrosurgical energy. The first actuator may be adapted to selectively adjust the flow of pressurized gas from the cylinder, and/or the second actuator may be adapted to selectively adjust the amount of electrosurgical energy that is delivered to the proximity of the active electrode. A pressure regulator may also be included which has a pressure relief valve in communication with the cylinder for relieving the pressure of the pressurized gas in the cylinder. There can also be included in the instrument a pressure relief valve which relieves the pressure of the pressurized gas, and there can be included a flow limiter which limits the flow of pressurized gas to the electrode.

In another embodiment, the electrosurgical instrument can include a valve which controls the flow of pressurized gas from the cylinder, at least one actuator which actuates the flow of pressurized inert gas from the cylinder to the active electrode, and which actuates the delivery of electrosurgical energy from the source to the active electrode. The at least one actuator may be movable from a first position to at least a subsequent position which operatively causes at least one electrical output signal to be transmitted to the flow control valve and to the source. Preferably, the at least one output signal is correlated to the degree of movement of the at least one actuator and the flow control valve and the source of electrosurgical energy are respectively adapted to deliver a corresponding flow of pressurized gas and a corresponding amount of electrosurgical energy to the active electrode. The electrosurgical instrument may also include at least one transducer electrically connected between the at least one actuator and the flow control valve and between the at least one actuator and the energy source. It is contemplated that this arrangement allows the at least one electrical output signal to be transmitted to the flow control valve and to the source.

In yet another embodiment, the electrosurgical instrument includes a valve which controls the flow of pressurized gas from the cylinder, wherein the first actuator and the second actuator are each selectively adjustable from a first position to at least a second position. It is contemplated that this movement operatively transmits a respective output signal to the flow control valve and to the source that is correlated to the amount of applied movement of the respective first and second actuators. In one particularly useful embodiment, the flow control valve and the source of electrosurgical energy each correspondingly supply an amount of gas and electrosurgical energy to the active electrode. At least one transducer can be electrically connected between the first actuator and the flow control valve and between the second actuator and the source to transmit the respective output signals to the respective flow control valve and source.

In other embodiments, the electrosurgical instrument can include a flow regulator and a sensor in electrical communication with the flow regulator. The sensor may be configured to sense a selected condition adjacent the distal end of the frame and automatically control the regulation of flow of pressurized gas to the active electrode. The instrument can include a sensor in electrical communication with a pressure relief valve which senses a selected condition at the surgical site and automatically activates the pressure relief valve to relieve the pressure of the pressurized gas in the cylinder, tube, receptacle and/or any other pressurized areas of the coagulator. The instrument can include a sensor in electrical communication with the second actuator which initiates delivery of electrosurgical energy from the source. The sensor in this instance may be configured to sense a selected condition at the surgical site and automatically modulate the delivery of energy to the active electrode.

In still other embodiments, the electrosurgical instrument may include a pressure regulator to reduce the pressure of the gas from its pressure level in the cylinder to one or more selected lower levels.

In particularly useful embodiments, the electrosurgical instrument is configured to produce inert gas enhanced electrosurgical fulguration, for example, to coagulate, coagulatively "paint" or produce a cutting effect in body tissue. The electrosurgical instrument can be configured and adapted for use in open, endoscopic and or laparoscopic applications. The electrosurgical instrument may also include a sensor which is electrically connected to a safety pressure relief valve which vents pressure from the cylinder before it is removed from the receptacle. Alternatively, the instrument may include a vent which is configured to allow the user to remove or alleviate the remainder of the pressure from the cylinder before or as the cylinder is being removed from the receptacle.

In still other useful embodiments, the active electrode can be located proximally of the port of the frame. The instrument can include a member that extends distally from the distal end of the frame, and the active electrode can be supported on the member in a position distal of the port.

The cylinder selectively engageable or removable (as used with, seated in or part of the electrosurgical instrument, or separately as a cylinder suitable for use, for example, in an electrosurgical instrument for medical applications) contains pressurized gas consisting of inert gas, preferably argon gas, or a mixture of gases and inert gases. The cylinder has a volume of about 100 cc or less. The pressure of the gas in the cylinder can be about 3000 psi or less. The cylinder preferably provides a flow rate of from about 0.2 liters/min. to about 4 liters/min., and/or a nominal flow rate of about 2 liters/min. The cylinder may be visibly coded, for example with color, to indicate a characteristic of the cylinder or of the pressurized gas, e.g., that it contains a particular inert gas or mixture of inert gases, or the flow rate of the pressurized inert gas, or the as-filled flow rate of the contained pressurized inert gas or that the cylinder is suitable for use in a particular electrosurgical instrument or procedure.

In still yet another embodiment, the cylinder contains pressurized gas and is suitable for use in an electrosurgical instrument for medical applications. The cylinder includes a body containing a pressurized gas consisting of inert gas, the body having a proximal end, a distal end and a seal which seals an outlet, wherein the volume of the cylinder is about 100 cc's or less. The cylinder can include: a safety pressure stop valve operative upon or after rupture of the seal to automatically prevent flow of the gas from the outlet when the cylinder is removed from the instrument; a safety pressure release valve to safely control release of cylinder internal gas overpressure; a gauge to continually measure and indicate to a user the volume of pressurized gas in the cylinder; a refill valve to allow refilling of the cylinder with inert pressurized gas without removing the cylinder from a hand-held instrument; and/or a flow control valve for selectively controlling gas flow from the cylinder through the outlet. The cylinder can include an indicator which indicates to the user that a characteristic of the pressurized gas in the cylinder is below a selected level.

In yet another embodiment, the present disclosure relates to an electrosurgical instrument for providing ionized inert gas to a surgical site, includes: a frame having a proximal end and a distal end, the distal end having a port for emitting ionized gas; a receptacle for seating a cylinder of pressurized inert gas therein, the frame housing a tube which channels the pressurized inert gas to the proximity of the electrode; an active electrode located adjacent the distal end of the frame, the electrode adapted to connect to a source of electrosurgical energy; and at least one actuator (e.g., a valve) actuates the flow of pressurized inert gas from the cylinder to the proximity of the active electrode and which actuates the delivery of electrosurgical energy from the source of electrosurgical energy to the active electrode for ionizing the pressurized inert gas for use at the surgical site.

It is envisioned that the at least one actuator may be adapted to actuate the release of pressurized inert gas from the cylinder prior to actuating the delivery of the electrosurgical energy from the source.

In one particularly useful embodiment, a first actuator is included which actuates the flow of pressurized inert gas from the cylinder and a second actuator which actuates delivery of the electrosurgical energy from the source of electrosurgical energy to the active electrode. Preferably, the first actuator is actuated prior to actuating the second actuator.

Preferably, the cylinder includes a sealed outlet and the actuator or valve includes a coupling which is configured to rupture the sealed outlet upon insertion of the cylinder into the receptacle. The valve may be configured to include a plenum positioned between the coupling and the channel which regulates flow of pressurized inert gas to the channel. Alternatively, the plenum may be disposed between the regulator portion of the regulator and valve and the proximal end of supply tube. The valve or valves may also be configured as one or more flow regulators or pressure regulators to regulate the flow of pressurized inert gas to the active electrode. The cylinder may be visibly coded to indicate a characteristic of at least one of the cylinder and the pressurized inert gas.

Preferably, the actuator (or actuators) is configured to actuate the flow of pressurized inert gas from the cylinder to the active electrode and actuate the delivery of electrosurgical energy from the electrosurgical energy source to the active electrode. The actuator may be selectively adjustable to control the flow of pressurized inert gas (either through the tube or from the cylinder) and the delivery of electrosurgical energy.

One or more pressure relief valves may be included to relieve the pressure of the pressurized inert gas from the tube or from the cylinder. In addition and or alternatively, a flow limiter may be included which limits the flow of pressurized inert gas to the active electrode.

In one particular embodiment, the electrosurgical instrument further includes: a flow regulator and a sensor in electrical communication with the flow regulator. The sensor may be configured to sense a selected condition and automatically control the regulation of flow of pressurized inert gas to the active electrode. Another sensor may be included in electrical communication with the pressure relief valve which senses a selected condition and automatically activates the pressure relief valve to relieve the pressure of the pressurized inert gas in the cylinder.

Preferably, the instrument is endoscopic and configured to produce inert gas-enhanced electrosurgical fulguration, coagulation, cauterization or coagulative painting. Preferably, the inert gas consists of argon or a mixture of one or more other inert gases. The instrument is preferably configured to include a cylinder having a volume of at least about 100 cc and a gas pressure of at least about 3000 psi.

The electrosurgical instrument may also be configured to include an indicator which indicates that a specific characteristic of the pressurized inert gas in the cylinder is different than a selected desired level. An extension member which supports the active electrode may be included which selectively extends from the distal end of the frame depending upon a particular purpose.

BRIEF DESCRIPTION OF THE DRAWINGS

FIG. 1 is a side schematic view of an electrosurgical coagulator according to the present disclosure;

FIG. 1A is an enlarged view of the encircled portion of FIG. 1;

DETAILED DESCRIPTION

Figure 2A:
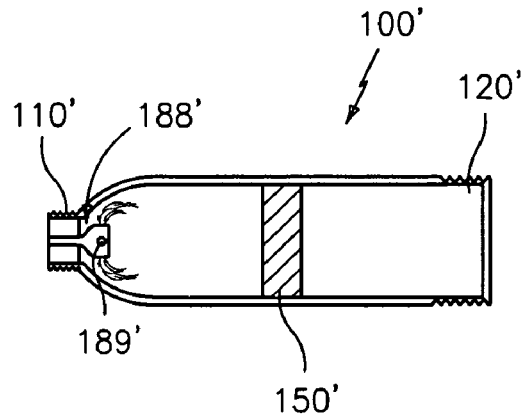
FIG. 2A is an enlarged, schematic sectional view of an alternate embodiment of a gas cartridge for use with the electrosurgical coagulator of FIG. 1 having a color coded identification band and a safety valve.

This application discloses embodiments of electrosurgical apparatus or instruments that are adapted for use with, and preferably include a self-contained supply of pressurized inert gas for providing ionizable gas to a surgical or operative site. FIG. 1 shows one embodiment of a gas-enhanced electrosurgical instrument, here, a gas coagulator, generally designated 10, for coagulating tissue. Preferably and as shown, coagulator 10 is dimensioned to be pencil-like or hand-held, including robotically, for use during open surgical procedures, however, it is envisioned that a similar instrument or coagulator may be configured, for example, with a pistol grip or handle dimensioned for laparoscopic or endoscopic surgical procedures. Although, the basic operating features of an open electrosurgical coagulator 10 are described herein, the same or similar operating features may be employed on or used in connection with a laparoscopic or endoscopic electrosurgical coagulator or instrument, manually or robotically operated, without departing from the scope of the present disclosure. The term "electrosurgical energy" herein refers to any type of electrical energy which may be utilized for medical procedures.

As shown in FIG. 1, coagulator 10 includes a frame, shown as an elongated housing 11, having a proximal end 12, a distal end 14 and an elongated cavity 15 extending therethrough, for supporting and/or housing a plurality of internal and/or external mechanical and electromechanical components thereon and therein. In this disclosure, as is traditional, the term "proximal" will refer to the end of coagulator 10 (or other element) which is closer to the user, while the term "distal" will refer to the end which is further from the user.

Distal end 14 of housing 11 includes a distal port 17 which is designed to emit, expel or disperse gas emanating from an elongated gas supply channel or tube 60 that in this embodiment runs generally longitudinally through frame or housing 11 of coagulator 10. Tube 60 is for supplying pressurized gas 50 to the proximity of an active electrode 350 located adjacent distal end 14 of housing 11. Preferably electrode 350 is proximal of port 17 such that the gas that is emitted from port 17 is ionized. Elongated housing 11 includes a receptacle 25, preferably adjacent its proximal end 12, which receptacle can be or be part of a unitary or integral handle portion 12a of housing 11. Receptacle 25 is dimensioned to securely engage and receive or seat a gas pressurized container, canister, cartridge or cylinder 100 therein. Cylinder 100 contains a surgical gas, preferably a noble or inert gas, or mixture of noble or inert gases. References herein to inert gas or gases are understood to include noble gas or gases. The preferred inert gas is argon. Cylinder 100 preferably is relatively small, single use and disposable. Preferably the cylinder is of standardized design and certified for transportation requirements. Moreover, it is preferable that the cylinder is designed and/or sized to be incompatible with other commercial products such as whip cream dispensers and the like which use nitrogen and $CO_2$ cartridges for other purposes. Details of gas cylinder 100 and its selective engagement with or connection to housing 11 are discussed in more detail below with respect to FIGS. 2A-2C.

Elongated gas supply tube 60 is adapted and dimensioned to channel or carry pressurized gas 50 from cylinder 100 through a regulator or valve 30 to or through distal end 14 of coagulator 10 for ionization, preferably prior to the gas emitting and dispersing from distal port 17. Regulator or valve 30 can be part of or attached to cylinder 100, housing 11, or actuator 31. It is envisioned that distal port 17 or distal end 14 may be configured to facilitate or promote the dispersion of the ionized gas plasma 50' from distal port 17 in a uniform and consistent manner. For example, distal end 14 may be tapered on one, both or all sides thereof to direct the ionized plasma 50' toward surgical or operative site 410. Alternatively, distal port 17 may be configured to disrupt or aggravate the dispersion or flow of gas plasma 50' exiting distal port 17 to enhance coagulation by creating a more turbulent gas flow. It is contemplated that many suitable devices, e.g., screws, fans, blades, helical patterns, etc., may be employed to cause gas plasma 50' to flow more or less turbulently or with other predetermined flow characteristics through tube 60 and/or out of distal port 17.

Elongated housing 11, preferably its proximal end 12, is connected, for example, by an electrical cable 310, to a source of electrosurgical energy generally designated ESU, e.g., an electrosurgical generator 300. As mentioned above, proximal end 12 includes a receptacle 25 which receives, securely engages and seats cylinder 100 therein. Receptacle 25 and/or cylinder 100 need not be, as in the case of a single use disposable instrument, but preferably is configured to allow cylinder 100 to be selectively removable and replaceable within receptacle 25. For example and as best shown in FIG. 1, proximal end 12 of elongated housing 11, or receptacle 25 may include a locking mechanism 40 which upon insertion of a cylinder 100 into receptacle 25 automatically (or manually) releasably locks the cylinder 100 securely within receptacle 25. By unlocking locking mechanism 40, cylinder 100 may be removed and replaced with another cylinder 100.

It is envisioned that the locking mechanism 40 may be any suitable device or arrangement, e.g., a collar or clamp which provides adequate lever advantage to set the cylinder 100 against its end seal. The collar or clamp is preferably designed to allow the cylinder to be disengaged from the seal but retained within the receptacle 25 until the remaining pressurized gas is vented or otherwise relieved. For example, the locking mechanism 40 may include two or more opposing spring clamps 42a, 42b which mechanically engage a corresponding one or more notches or cut outs 120a, 120b formed in the outer surface of gas cylinder 100. As can be appreciated, upon insertion of cylinder 100 into receptacle 35, the spring clamps 42a, 42b are positioned to allow entry of cylinder 100 into receptacle 25 until the spring clamps engage the notches 120a, 120b. It is envisioned that a locking mechanism 40 with spring clamps can be configured and adapted for releasably locking and quickly releasing the locking of cylinder 100 in receptacle 25.

Preferably, the relative positioning and mechanical engagement of spring clamps 42a, 42b in notches 120a, 120b fully seats cylinder 100 within the receptacle such that a distal end 110 of cylinder 100 fully engages valve 30. The full seating of cylinder 100 in receptacle 25 can effect piecing or puncturing of the sealed distal end 110 of gas cylinder 100. Upon opening or actuation of valve 30, gas 50 is dispersed to elongated supply tube 60 as explained below.

A variety of other locking mechanisms may be utilized to secure gas cylinder 100 to or within receptacle 25. For example, the distal end 110 of cylinder 100 of FIG. 1a may be configured, e.g., threaded (as shown as 110' in FIG. 2A) to threadedly engage valve 30. Alternatively, as also shown in FIG. 2A, the proximal end of cylinder 100' may include threads 120' which threadably engage the interior of receptacle 25 (not shown). In this instance it may be advantageous to include or provide a rubber O-ring or washer in the proximity of the threads to protect against undesirable gas leakage.

Alternatively, proximal end 12 of housing 11 may be adapted to have an externally threaded collar or sleeve that extends axially outwardly and have an internally threaded screw closure cap. With a cylinder seated in receptacle 25, the screw closing of the cap would push cylinder 100 distally against the bias of a spring onto an axially disposed piercing member to thereby break the seal at the distal tip of the cylinder. Removal of the closure cap would permit removal and replacement of the cylinder. The cap can be adapted to safely vent pressurized gas from the interior of the receptacle 25 should the seal on the distal end of the cylinder be lost or damages thus preventing the receptacle from bursting in the event of an internal overpressure. Additionally, the cap may be configured to include a pressure regulator or valve to control flow through seal opening. As can be appreciated, this safety feature may be designed to limit the flow from the cylinder and protect the user if the cylinder becomes damaged during handling. Other locking mechanisms are also envisioned, for example an over-the-center lever arrangement for pulling a yoke around the end of cylinder 100, snap locks, spring locks on the cylinder 100, locking levers, bayonet style locks, and locking dials or tabs, etc.

The cylinder 100 may also include various ergonomically friendly features such as rubber gripping elements or contoured walls to facilitate insertion into the housing 11 and handling especially during wet operative conditions. Additionally and as described in more detail below, the cylinder may be color coded to specify any or a combination of the following: cylinder contents (gas type and amount); initial pressure reading prior to activation; a specific flow rate; or specify use for a given procedure.

Electrosurgical instrument 10 includes at least one actuator, e.g., a dial or button, generally designated 31, for actuating and preferably selectively adjusting the flow of pressurized inert gas 50 from cylinder 100 to the proximity of active electrode 350, and for actuating and preferably selectively adjusting the delivery of electrosurgical energy from the source, i.e., from generator 300, to the active electrode 350 for ionizing the inert gas for use at the surgical site 410. Actuator 31 can also operate as the actuator for actuating delivery of electrosurgical energy from the source. Actuator 31 may be referred to herein as the first actuator. It is envisioned that instead of being located in housing 11, one or more of the actuators, regulators and/or valves described herein may be located in a foot switch appropriately connected to coagulator 10.

Electrosurgical instrument or coagulator 10 can also include a second actuator, here shown as a button-like trigger 20, for actuating the delivery of electrosurgical energy from the source, e.g., from generator 300, through cable 310 and leads 322, 330 to the active electrode 350 for ionizing the inert gas for use at the surgical site 410. Trigger 20 can be attached to or mounted, for example, on or atop or through elongated housing 11. Trigger 20 may be any type of known trigger, e.g., a rocker switch, a handswitch, a footswitch, a slide switch, a dial, a button, a lever, etc., which, upon actuation thereof, electrically communicates with electrosurgical generator 300 to allow the selective delivery of electrosurgical energy to active electrode 350.

Active electrode 350 can be attached to or mechanically engaged with the distal end of the housing and positioned adjacent to or at an operating site 410. Preferably, active electrode 350 is positioned adjacent the distal end of frame or housing 11, preferably between the distal end of tube 60 and distal port 17, although the active electrode can be located just to the exterior of port 17. For example, active electrode 350 can be mounted to an elongated member that is supported within housing 11 and that extends outside of the housing, such that the electrode is positioned just outside of the port. Active electrode 350 need not be as shown. It can be a conductive elongated member in the form of a blade, needle, snare or ball electrode that extends from an electrosurgical instrument and that is suitable, for example, for fulguration, i.e., coagulation, cutting or sealing tissue.

As shown and in most monopolar electrosurgical systems, a return electrode or pad 370 is typically positioned under the patient and connected to a different electrical potential on electrosurgical generator 300 via cable 360. During activation, return pad 370 acts as an electrical return for the electrosurgical energy emanating from electrosurgical coagulator 10. It is envisioned that various types of electrosurgical generators 300 may be employed for this purpose, such as those generators sold by Valleylab, Inc.—a division of Tyco Healthcare Group LP, of Boulder, Colo.

It is envisioned that trigger 20, upon actuation thereof, is designed to energize electrode 350 in a simple "on/off" manner, e.g., when the trigger is depressed (or otherwise moved or manipulated, e.g., twisted (dial switch), rocked (rocker switch), or slid (slide switch)). Alternatively, it is contemplated that the electrical intensity from generator 300 may be selectively regulated by trigger 20, such that the user can alter the electrosurgical effect at operative site 410. For example a pressure sensitive trigger or regulator may be utilized to control the amount of electrosurgical energy that is conducted to electrode 350 which, as described below with respect to the operation of coagulator 10, effects coagulation of tissue 400. Triggers and actuators that are contemplated include those such as described in commonly-owned U.S. Provisional Application Ser. No. 60/424,352 and commonly-owned U.S. application Ser. No. 10/251,606, the entire contents of each of which are incorporated by reference herein, without intention of being limited to the same.

U.S. application Ser. No. 10/251,606, now publication No. 04-0092927 discloses an electrosurgical instrument having variable controls, a housing, and an electrocautery blade or electrode extending from the housing and connected to a source of electrosurgical energy. An actuator button supported on the housing is movable, e.g., depressed, or rocked or slid, from a first position to at least a subsequent position, preferably to a series of discrete subsequent positions wherein each subsequent position corresponds to a specific amount of energy being transmitted to the blade. Preferably, a transducer, e.g., a pressure transducer, or other suitable circuit element, is electrically connected between the activation button and the source of electrosurgical energy. The transducer is configured to transmit an electrical output signal, preferably a range of output signals, to the energy source correlating to the selected movement or position(s) of the activation button. The source correspondingly supplies an amount or range of electrosurgical energy emission to the blade dependent upon the electrical output signal(s).

The above actuator and selectively adjustable system can be employed using at least one actuator, actuator 31, for actuating and preferably selectively adjusting the flow of pressurized gas from cylinder 100, e.g., via regulator and valve 30, and for actuating and preferably selectively adjusting delivery of energy from the source. Such can be achieved by employing, for example, a suitable transistor that produces a signal or two signals or different sets of output signals based on movement of the actuator button. The signal (or one signal or set of signals) is sent to and is suitable for actuating actuator 31 or regulator and valve 30 to actuate movement-correlated corresponding selectively adjusted flow of gas from the cylinder. The signal (or the other signal or set) is sent to and is suitable for actuating trigger 20 to deliver energy from the source. A similar suitable actuator system can be employed with one transistor to actuate a first actuator, actuator 31, for actuating and preferably selectively adjusting the flow from cylinder 100, and a second transistor to actuate a second actuator, trigger 20, for actuating and preferably selectively adjusting delivery of energy from the source. It is envisioned that instead of being located in housing 11, trigger 20 can be located in a foot switch appropriately connected to electrosurgical generator 300 and coagulator 10.

It is contemplated that the at least one actuator, e.g., actuator 31, is adapted or operated to actuate the release of pressurized gas 50 prior to actuating the delivery of electrosurgical energy from generator 300. When there is a first actuator and a second actuator, it is contemplated that the instrument or coagulator includes one or more elements, e.g., circuitry, or mechanical or electromechanical mechanism(s), for timing the flow of gas from cylinder 100 and the delivery of energy to the electrode. Preferably, the first actuator is activated prior to the activation of the second actuator.

It is also contemplated that trigger 20 (or generator 300) may cooperate with one or more sensors 365 which can be attached to instrument 10, housing 11 or electrode 350 and which, for example, continually measures or monitors a condition at operative site 410, e.g., the amount of tissue coagulation, and relays the information back to generator 300 or trigger 20. For example, a control system or a safety circuit (not shown) may be employed which automatically (e.g., through a shut-off switch) reduces pressure or partially closes valve 30 if an obstruction is indicated. Alternatively or in addition, the safety circuit may be configured to cut off the energy to tissue 400 and/or activate or release a pressure relief valve (e.g., a safety release valve generally designated 367) to release the pressure of the pressurized gas based upon a sensed condition (e.g., an embolic condition or concern) by a sensor 365 or by the surgeon. It is also envisioned that based upon the sensed condition, gas cylinder 100, e.g., by valve 30, can be partially modulated, inactivated, ejected (or released) from engagement with valve coupling 32, or valve 30 may be automatically fully de-activated or closed. Alternatively, sensor 365 may provide feedback to trigger 20 or generator 300 to optimize coagulation of the tissue 400 based upon distance from the tissue deduced from the measured back pressure in supply tube 60, based upon tissue type or based upon tissue response. A second sensor 321 may be employed to measure the flow of gas 50 through gas supply tube 60, and may be electrically connected to a flow regulator, e.g., valve 30, to automatically regulate the flow of gas from cylinder 100 to electrode 350.

As best shown in FIG. 1, actuator 31 preferably includes regulator and valve 30 which is mounted to and through elongated housing 11 and which can be dimensioned to mechanically engage (and preferably also puncture or otherwise engage and open) the sealed outlet at distal end 110 of selectively removable gas cylinder 100. Gas cylinder 100 can be removable in a reusable or disposable version of the instrument. In one particularly useful embodiment, the mechanical engagement and securement of gas cylinder 100 and valve 30 involves a quick-release type mechanism or other simple attachment mechanism which can be employed on and/or or as part of cylinder 100, receptacle 25 and/or housing 11 to enable the user to quickly and accurately engage and disengage and remove and replace gas cylinder 100. For example, various springs, levers, latches, slides and frictional engagement members, (not shown) may be employed to facilitate loading and quick removal of cylinder 100. As mentioned above, locking mechanism 40 may be employed to permanently or releasably secure cylinder 100 within receptacle 25.

Actuation of actuator 31 preferably activates regulator and valve 30. Regulator and valve 30 selectively controls or regulates the flow of gas from cylinder 100 to electrode 350. Regulator and valve 30 preferably includes a cylinder interface or coupling 32 and a plenum 34. Actuator 31 or regulator and valve 30 selectively adjusts plenum 34 to regulate, preferably selectively, the amount or flow of gas 50 from gas cylinder 100, to supply tube 60 and to electrode 350.

It is envisioned that actuator 31 may be incrementally adjustable (i.e., rotatable, slideable or pressure sensitive) to provide tactile feedback to the user relating to the flow of gas 50. As can be appreciated, plenum 34 is disposed between the regulator portion of the regulator and valve 30 and the proximal end 62 of supply tube 60. As mentioned above, coupling 32 mechanically engages (e.g., threadably engages, snap fits, friction-fits, slide fits, spring mounts, bayonets, or otherwise) cylinder 100, seals the juncture with cylinder 100, and preferably also breaks, pierces or otherwise opens the sealed distal end or outlet of cylinder 100 upon insertion of the cylinder 100 into receptacle 25. Although it is preferred that actuator 31 include regulator and valve 30, regulator and valve 30 can include actuator 31. Regulator and valve 30 may be referred to herein as a first flow regulator for selectively regulating the flow of pressurized gas from cylinder 100.

In one embodiment, coagulator 10 can include separate pressure regulators, valves and/or flow regulators which are separated and spaced down the length of the coagulator 10. For example, a second flow regulator, e.g., "FR2" may be included which selectively regulates the flow of pressurized gas to electrode 350. In yet another embodiment, coagulator 10 can include a pressure regulator, e.g., "PR", for regulating the pressure of the pressurized gas that flows to electrode 350. Valve 30 may include a pressure regulator having a pressure relief valve in communication with cylinder 100 for regulating and/or relieving the pressure of the pressurized gas in the cylinder. Coagulator 10 preferably includes a flow limiter. For example, valve 30 may include a flow limiter for limiting the flow of pressurized gas to electrode 350 to a selected level. In one particularly useful embodiment, a pressure relief valve or "burp valve" may be included which is disposed proximal to the flow limiter or plenum to permit gas to escape from the channel 60 thereby preventing a build-up of pressure at opening 17 as a result of partial of full occlusion of opening 17. A flue 430 (see FIG. 1) may be included which transfers the relieved gas flow to the proximal end of the coagulator 10.

Preferably, distal end 110 of cylinder 100 is hermetically sealed when and after it is mounted to and mechanically engaged with coupling 32 to avoid undesirable gas leakage from the mechanical connection. The end seal may be formed through metal-to-metal contact, by an elastomeric land at the face 110 of cylinder 100 or an elastomeric ring encircling cylinder 100. As can be appreciated, various rubber seals, gaskets, flanges or the like (not shown) may be employed to accomplish this purpose.

It is envisioned and preferred that valve 30 be opened, e.g., manually, to a desired flow rate prior to activation of electrode 350 to ionize the plasma to coagulate tissue 400. The same button, actuator or lever that actuates the delivery of energy would also activate regulator and valve 30 and the flow of gas. For example, the movement of a lever would actuate regulator and valve 30 and the flow of gas prior to continued movement of the lever to actuate delivery of energy from the generator 300. It is also contemplated that actuator 31 or valve 30 may be automatically regulated to communicate with trigger 20 and be automatically controlled by activation of trigger 20. For example, the user may select a flow rate by actuating actuator 31 (which may include a visual indicator or the like to allow the user to readily determine flow rate) such that upon actuation of trigger 20, regulator and valve 30 initiates the flow of gas 50 through tube 60 to the an ignition point 355 proximate electrode 350. Electrode 350 can, in turn, be activated to ionize the gas 50 and force the ionized gas plasma 50' at the tissue or operating site 410. Alternatively, actuation of actuator 31 or regulator and valve 30 can automatically activate actuation of trigger 20 and flow of electrosurgical energy to electrode 350.

Preferably, after actuation of trigger 20 and initiation of gas flow to ignition point 335, the ignition of the electrode 350 is delayed either mechanically, electro-mechanically or utilizing delay circuitry or a delay algorithm to preferably enhance delivery of plasma 50' to operating site 410. As can be appreciated, the delay circuitry or algorithm may be incorporated in trigger 20, valve 30 or generator 300.

During use, ionizable gas 50 is supplied under pressure from gas cylinder 100 to regulator and valve 30 (or simply a flow regulator) and, upon selective actuation of actuator 31, the gas flows to ignition point 335 near electrode 350 where gas 50 is ionized into a gas plasma 50' before being distributed, dispersed or dispensed out of distal end 17 to operating site 410. During use, the user may selectively alter the gas flow rate and/or the intensity of the energy emanating from electrode 350 to meet a desired surgical effect.

Preferably, gas cylinder 100 is relatively small and contains an appropriate or sufficient amount gas 50 for a given surgery of short duration. Cylinder 100 preferably is for single use, and is disposable. It may be replaced as needed during the surgical procedure if it requires a longer or different gas application than provided by a single gas cylinder. As can be appreciated, different gas cylinders 100 may be utilized for different surgeries which have different gas requirements, e.g., in terms of types, amounts, pressures and/or flow rates.

The gas pressure of cylinders 100 preferably is about 3000 psi or less. Gas cylinders 100 preferably have a volume of about 100 cc's or less.

Cylinders 100 containing about 4 liters of gas and a flow time of about 2 minutes have been found suitable for a typical coagulation procedure. For such procedures, the flow rate provided by the cylinder can range from about 0.2 liters/min. to about 4 liters/min, and the nominal flow rate may be about 2 liters/min. It is envisioned that cartridge 100 may be pre-configured to deliver gas at a predefined flow rate, and coagulator 10 may be configured without a flow regulator or flow valve 30 in or on elongated housing 11. Instead, elongated housing 11 may simply include an "open" and "close" switch (not shown) which blocks or releases the flow of gas from the gas cylinder 100 depending upon the position of the switch. As a result thereof, when opened, coagulator 10 relies on the predetermined flow rate of the gas 50 exiting the gas cylinder 100 under pressure.

The gas flow rate employed is dependent upon factors such as the instrument being used and/or the type of surgery or procedure to be performed. Different gas cartridges, e.g., cylinder 100', can be pre-marked or coded, e.g., visibly, with a color, e.g., a colored band 150' (see FIG. 2A) to indicate a specific gas, as-filled flow rate or suitability for a particular instrument, procedure or application. Thus, a user may pick the appropriate color which specifically relates to a desired specific gas, flow rate and intended surgical use. Since cylinders 100 are easily replaceable, during surgery the user may opt to replace a cylinder 100 with a different cylinder 100' with a different flow rate (different color band 150'). Cylinder 100 may include a knob, e.g., 100a at the proximal end of the cylinder to facilitate manipulation of the cylinder.

FIG. 2A shows an embodiment of a gas cylinder 100' which includes a safety release pressure stop valve 188' which is designed to automatically prevent flow of gas from, cylinder 100' when the cylinder is removed. More particularly, upon release of the cylinder 100' from coupling 32, a ball 189' (in a ball check valve) or some other movable obstruction automatically moves distally to block the passage of gas 50 through distal end 110' of the cylinder 100'. Upon insertion or engagement of the cylinder 100' into coupling 32, a pin or other protruding element (not shown) forces ball 189' proximally to allow the release of gas 50 from cylinder 100'. As can be appreciated, many different types of release pressure stops may be employed to accomplish the same or similar purpose and the above-described release pressure stop valve 188' is only one example. It is contemplated that cylinder 100 or the like, e.g., 100''', can include a safety pressure release valve "SPRV" to vent the gas prior to or when an active cylinder 100 is removed from receptacle 25 and/or to safely control release of cylinder internal gas overpressure. It is also contemplated that coagulator 10, e.g., receptacle 25, can include a pressure relief valve 440 in communication with cylinder 100 for relieving the pressure of the pressurized gas in the cylinder.

Figure 2B:
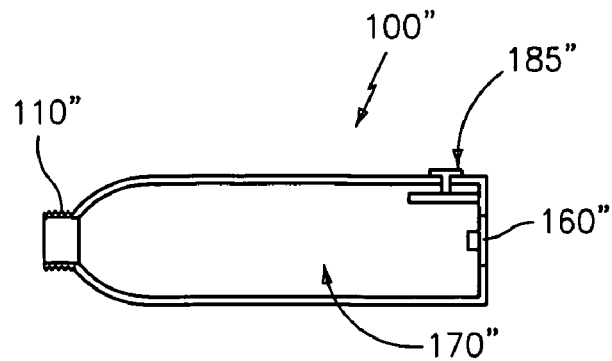
FIG. 2B is an enlarged, schematic sectional view of a gas cartridge for use with the electrosurgical coagulator of FIG. 1 having a volume gauge and a refilling port.

As best shown in FIG. 2B, an embodiment of gas cylinder 100" may include a gauge 185" which measures and indicates the amount of pressurized gas left in cylinder 100" at any given time. A visual or audible indicator or sensor (not shown), may be employed to alert the user of a low gas condition. Gas cylinder 100" may also include a fill port or refill valve 160" which enables the user to selectively refill interior 170" of gas cylinder 100" without removing the cylinder from within receptacle 25 of instrument 10.

Figure 2C:
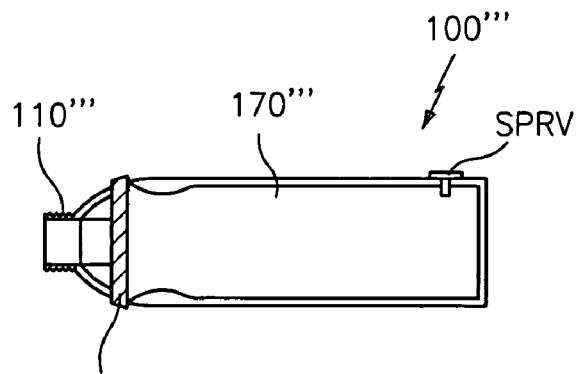
FIG. 2C is an enlarged, schematic sectional view of a gas cartridge for use with the electrosurgical coagulator of FIG. 1 having a flow regulator.

FIG. 2C shows another embodiment of gas cylinder 100''' which includes a valve 180''' disposed thereon which allows a user to selectively regulate gas flow from interior chamber 170''' through distal end 110''' and to coagulator 10. As such, a valve would not necessarily be needed within coagulator 10 and the user can selectively regulate gas 50 by rotating (or otherwise adjusting) valve 180''' as needed.

Figure 3A:
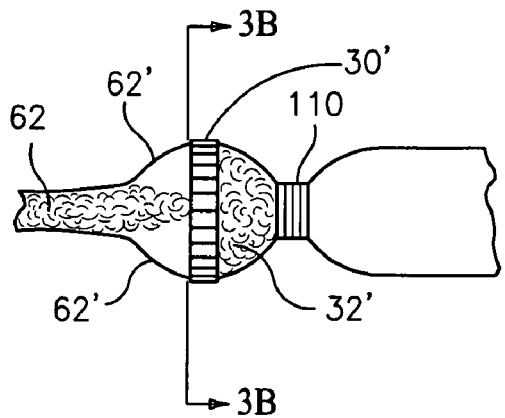
FIG. 3A is a greatly-enlarged, schematic side view of an iris-like flow regulator for use with the electrosurgical coagulator of FIG. 1.
Figure 3B:
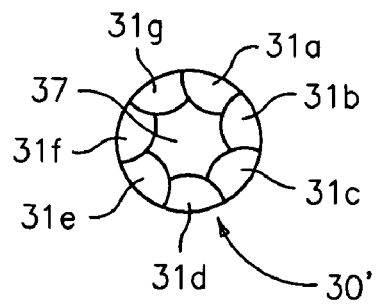
FIG. 3B is a cross sectional view of the iris-like flow regulator taken along line 3B-3B of FIG. 3A.

FIGS. 3A and 3B show an embodiment of a flow control valve, here shown as a rotary iris-like valve 30', which may be utilized within coagulator 10 (or with the gas cylinder 100''' as mentioned above) for selectively controlling the flow of pressurized gas from the cylinder. Iris valve 30' is preferably disposed between a coupling 32' and a flared portion 62' of proximal end 62 of supply tube 60. Upon rotation of iris valve 30' in a first direction, a series of interleaved portions 31a-31g move to radially reduce or condense the dimensions of passageway or opening 37 to limit gas flow therethrough and to the flared portion 62' of gas supply tube 60. Upon rotation of iris valve 30' in the opposite direction, the interleaved portions 31a-31g move to radially expand the dimensions of opening 37, enhancing gas flow therethrough and to the flared portion 62' of the supply tube 60.

It is envisioned that a corona return electrode or corona start electrode (not shown, but known in the art) may be utilized with electrode 350 to initiate a plasma arc. The corona return electrode may be placed on or within housing 11 located near distal end 14 or distal port 14. The corona return electrode is electrically connected to return path 360 of electrosurgical generator 300. The function of the corona return electrode is to establish a non-uniform electrical field with active electrode 350. The non-uniform electric field will cause the formation of a corona near active electrode 350, which will thereby aid in the ignition of gas 50 as it flows out of distal port 17 of the housing 11. Preferably, a dielectric member (not shown) is positioned to separate active electrode 350 from the corona return electrode.

It is also envisioned that the coagulator 10 may be configured to include a two-stage regulator (not shown) instead of a burp valve. In particular, this may be particularly advantageous for use with a laparoscopic device wherein the gas flow may be affected by insufflation pressure in the operating cavity.

From the foregoing and with reference to the various drawings, those skilled in the art will appreciate that not only can the electrosurgical instrument of the present disclosure, an embodiment of which is coagulator 10, be used to arrest bleeding tissue, but embodiments of the present disclosure can also be employed for desiccating surface tissue, eradicating cysts, forming eschars on tumors or thermically marking tissue. Those skilled in the art will also appreciate that certain modifications can also be made to the present disclosure without departing from the scope of the present disclosure.

For example, while several embodiments of the coagulator show an internally mounted cylinder 100 which fits within receptacle 25 of housing 11, it is envisioned that an externally mounted cylinder may be used to accomplish the same purpose. Moreover, although it is preferable to utilize argon as the ionizable gas for promulgating coagulation of the tissue, in some cases it may be preferably to use another ionizable gas or a combination of ionizable gases to effect the same or, a similar or different result.

Although the presently described coagulator employs a trigger which is designed to be hand-activated, including robotically, it is envisioned that a foot switch (not shown) may be utilized to activate the ionizing electrode. Moreover, it is also contemplated that the footswitch may be configured to house the gas cylinder therein. For example, the footswitch may include a receptacle for securely receiving a gas cylinder therein and a supply hose for transporting the flow of gas to and through the coagulator. As can be appreciated, this may be particularly advantageous since a larger gas cartridge may be provided in the foot switch than in the frame or handle of a hand held device, thus reducing the number of times that the user would have to replace the gas cartridge of the hand held device (if at all) during prolonged use. The gas supply hose may be attached to the electrosurgical cable which attaches to the proximal end of the coagulator to limit tangling.

It is also envisioned that the footswitch may not only contain the trigger for energizing the ionizing electrode but may also be configured to itself be or contain the actuator for releasing the flow of gas through the supply tube and to the surgical site.

Moreover, although shown as a pencil-like electrosurgical instrument or coagulator in the drawings, it is envisioned that the coagulator may include a pistol grip-like handle which enables the user to handle the instrument like a pistol. It is also contemplated that the cylinder may be dimensioned for selective engagement (i.e., insertion) within and disengagement (i.e., release) from the handle. Alternatively, the handle may be selectively pivotable for handling the coagulator in different orientations, e.g., from an offset position relative to the housing for handling the coagulator in pistol-like fashion to a generally aligned orientation for handling the coagulator like a pencil.

It is envisioned that the electrosurgical instrument or coagulator and the cylinders may be completely disposable or the coagulator may be reposable and the cylinders disposable. Moreover, the mechanically engaging distal end of the cylinders may be designed for easy retrofits onto exiting coagulators. It is envisioned that instrument 10, for example, housing 11 or actuator 31 can include a second flow regulator (not shown) to regulate the flow of gas to active electrode 350.

It is envisioned that instrument 10, for example, housing 11 or actuator 30 can include a second flow regulator, "FR2", to regulate the flow of gas to active electrode 350.

There have been described and illustrated herein several embodiments of a coagulator for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical instrument for providing ionized inert gas to a surgical site, comprising:
    a frame having a proximal end and a distal end, the distal end having a port for emitting ionized gas;
    a receptacle for seating a cylinder of pressurized inert gas within the frame, the frame housing a tube which channels the pressurized inert gas to the proximity of the electrode;
    an active electrode located adjacent the distal end of the frame, the electrode adapted to connect to a source of electrosurgical energy;
    at least one actuator which actuates the flow of pressurized inert gas from the cylinder to the proximity of the active electrode and which actuates the delivery of electrosurgical energy from the source of electrosurgical energy to the active electrode for ionizing the pressurized inert gas for use at the surgical site;
    a selectively releasable locking mechanism configured to releasably engage the cylinder upon insertion of the cylinder into the receptacle; and
    a first flow regulator which selectively regulates the flow of pressurized inert gas from the cylinder upon actuation.

2. The electrosurgical instrument according to claim 1, wherein the at least one actuator is adapted to actuate the release of pressurized inert gas from the cylinder prior to actuating the delivery of the electrosurgical energy from the source.

3. The electrosurgical instrument according to claim 1, wherein a first actuator is included which actuates the flow of pressurized inert gas from the cylinder and a second actuator which actuates delivery of the electrosurgical energy from the source of electrosurgical energy to the active electrode.

4. The electrosurgical instrument according to claim 3, wherein the first actuator is actuated prior to actuating the second actuator.

5. The electrosurgical instrument according to claim 4, wherein the first actuator which actuates the flow of pressurized gas from the cylinder is adapted to selectively adjust the flow of pressurized gas from the cylinder.

6. The electrosurgical instrument according to claim 4, wherein the second actuator which actuates the delivery of electrosurgical energy from the electrosurgical energy source is adapted to selectively adjust the amount of electrosurgical energy that is delivered to the active electrode.

7. The electrosurgical instrument according to claim 3, wherein the first actuator which actuates the flow of pressurized inert gas includes a valve.

8. The electrosurgical instrument according to claim 7, wherein the cylinder includes a sealed outlet and the valve includes a coupling which is configured to rupture the sealed outlet upon insertion of the cylinder into the receptacle.

9. The electrosurgical instrument according to claim 7, wherein the valve includes a plenum positioned between a coupling and the tube which regulates flow of pressurized inert gas to the channel.

10. The electrosurgical instrument according to claim 7, wherein the valve is also a flow regulator which regulates the flow of pressurized inert gas to the active electrode.

11. The electrosurgical instrument according to claim 7, wherein the valve also includes a pressure regulator which regulates the pressure of the pressurized inert gas.

12. The electrosurgical instrument according to claim 3, further comprising:
    a sensor in electrical communication with the second actuator which actuates delivery of electrosurgical energy from the source, the sensor being configured to sense a selected condition and automatically modulate the delivery of energy to the active electrode.

13. The electrosurgical instrument according to claim 1, wherein the at least one actuator which actuates the flow of pressurized inert gas includes a valve.

14. The electrosurgical instrument according to claim 1, further comprising:
    a pressure regulator which regulates the pressure of the pressurized inert gas flowing to the active electrode.

15. The electrosurgical instrument according to claim 14, wherein the pressure regulator includes a pressure relief valve in communication with the cylinder which relieves the pressure of the pressurized inert gas in the cylinder.

16. The electrosurgical instrument according to claim 1, further comprising:
    a second flow regulator which selectively regulates the flow of pressurized inert gas to the active electrode.

17. The electrosurgical instrument according to claim 1, further comprising:
    a pressure relief valve for relieving the pressure of the pressurized inert gas.

18. The electrosurgical instrument according to claim 17, further comprising:
a sensor in electrical communication with the pressure relief valve which senses a selected condition and automatically activates the pressure relief valve to relieve the pressure of the pressurized inert gas in the cylinder.

19. The electrosurgical instrument according to claim 1, further comprising:
a flow limiter which limits the flow of pressurized inert gas to the active electrode.

20. The electrosurgical instrument according to claim 1, wherein the instrument is configured to produce inert gas-enhanced electrosurgical fulguration.

21. The electrosurgical instrument according to claim 1, wherein the instrument is configured to coagulate body tissue.

22. The electrosurgical instrument according to claim 1, wherein the instrument is configured and adapted for use in an endoscopic application.

23. The electrosurgical instrument according to claim 1, wherein the instrument is configured and adapted for use in a laparoscopic application.

24. The electrosurgical instrument according to claim 1, wherein the inert gas consists of argon.

25. The electrosurgical instrument according to claim 1, wherein the inert gas consists of a mixture of inert gases.

26. The electrosurgical instrument according to claim 1, wherein the cylinder has a volume of at least one of approximately 100 cc or greater.

27. The electrosurgical instrument according to claim 1, wherein the pressure of the pressurized inert gas in the cylinder is at least one of approximately 3000 psi and greater.

28. The electrosurgical instrument according to claim 1, further comprising:
an indicator which indicates that a characteristic of the pressurized inert gas in the cylinder is different than a selected desired level.

29. The electrosurgical instrument according to claim 1, wherein the cylinder is visibly coded to indicate a characteristic of at least one of the cylinder and the pressurized inert gas.

30. The electrosurgical instrument according to claim 1, further comprising:
a member which supports the active electrode and which is selectively extendable from the distal end of the frame.

31. An electrosurgical instrument for providing ionized inert gas to a surgical site, comprising:
a frame having a proximal end and a distal end, the distal end having a port for emitting ionized gas;
a receptacle for seating a cylinder of pressurized inert gas within the frame, the frame housing a tube which channels the pressurized inert gas to the proximity of the electrode;
an active electrode located adjacent the distal end of the frame, the electrode adapted to connect to a source of electrosurgical energy;
at least one actuator which actuates the flow of pressurized inert gas from the cylinder to the proximity of the active electrode and which actuates the delivery of electrosurgical energy from the source of electrosurgical energy to the active electrode for ionizing the pressurized inert gas for use at the surgical site; and
a selectively releasable locking mechanism configured to releasably engage the cylinder upon insertion of the cylinder into the receptacle, wherein the at least one actuator which actuates the flow of pressurized inert gas from the cylinder to the active electrode and which actuates the delivery of electrosurgical energy from the electrosurgical energy source to the active electrode is selectively adjustable to control the flow of pressurized inert gas and the delivery of electrosurgical energy.

32. An electrosurgical instrument for providing ionized inert gas to a surgical site comprising:
a frame having a proximal end and a distal end, the distal end having a port for emitting ionized gas;
a receptacle for seating a cylinder of pressurized inert gas within the frame, the frame housing a tube which channels the pressurized inert gas to the proximity of the electrode;
an active electrode located adjacent the distal end of the frame, the electrode adapted to connect to a source of electrosurgical energy;
at least one actuator which actuates the flow of pressurized inert gas from the cylinder to the proximity of the active electrode and which actuates the delivery of electrosurgical energy from the source of electrosurgical energy to the active electrode for ionizing the pressurized inert gas for use at the surgical site;
a selectively releasable locking mechanism configured to releasably engage the cylinder upon insertion of the cylinder into the receptacle;
a flow regulator; and
a sensor in electrical communication with the flow regulator, the sensor being configured to sense a selected condition and automatically control the regulation of flow of pressurized inert gas to the active electrode.

33. An electrosurgical instrument for providing ionized inert gas to a surgical site, comprising:
a flame having a proximal end and a distal end, the distal end having a port for emitting ionized gas;
a receptacle for seating a cylinder of pressurized inert gas within the frame, the frame housing a tube which channels the pressurized inert gas to the proximity of the electrode;
an active electrode located adjacent the distal end of the frame, the electrode adapted to connect to a source of electrosurgical energy;
at least one actuator which actuates the flow of pressurized inert gas from the cylinder to the proximity of the active electrode and which actuates the delivery of electrosurgical energy from the source of electrosurgical energy to the active electrode for ionizing the pressurized inert gas for use at the surgical site;
a selectively releasable locking mechanism configured to releasably engage the cylinder upon insertion of the cylinder into the receptacle; and
a sensor for sensing a condition, the sensor being electrically connected to a safety pressure relief valve which vents pressure from the cylinder before the cylinder is removed from the receptacle.

* * * * *